(12) United States Patent
Boghossian

(10) Patent No.: US 9,950,850 B2
(45) Date of Patent: *Apr. 24, 2018

(54) THERAPEUTIC RINSE

(71) Applicant: Juliet Agatha Boghossian, Glendale, CA (US)

(72) Inventor: Juliet Agatha Boghossian, Glendale, CA (US)

(*) Notice: Subject to any disclaimer, the term of this patent is extended or adjusted under 35 U.S.C. 154(b) by 527 days.

This patent is subject to a terminal disclaimer.

(21) Appl. No.: 14/258,978

(22) Filed: Apr. 22, 2014

(65) Prior Publication Data

US 2014/0224692 A1 Aug. 14, 2014

Related U.S. Application Data

(63) Continuation-in-part of application No. 13/372,356, filed on Feb. 13, 2012, now Pat. No. 8,709,505.

(Continued)

(51) Int. Cl.
| | |
|---|---|
| *A61K 35/644* | (2015.01) |
| *A61K 36/484* | (2006.01) |
| *B65D 81/34* | (2006.01) |
| *A61J 1/14* | (2006.01) |
| *A61K 33/14* | (2006.01) |
| *A61K 31/19* | (2006.01) |

(Continued)

(52) U.S. Cl.
CPC ........ *B65D 81/3484* (2013.01); *A61J 1/1412* (2013.01); *A61K 8/19* (2013.01); *A61K 8/922* (2013.01); *A61K 8/97* (2013.01); *A61K 31/19* (2013.01); *A61K 33/14* (2013.01); *A61K 35/644* (2013.01); *A61K 36/185* (2013.01); *A61K 36/484* (2013.01); *A61K 36/53* (2013.01); *A61K 36/81* (2013.01); *A61K 45/06* (2013.01); *A61K 9/0056* (2013.01); *A61K 9/08* (2013.01); *A61K 2800/242* (2013.01); *A61M 31/00* (2013.01)

(58) Field of Classification Search
CPC .... A61K 36/185; A61K 36/484; A61K 36/53; A61K 35/644
USPC ........................................ 424/725, 757, 539
See application file for complete search history.

(56) References Cited

U.S. PATENT DOCUMENTS 6,051,236 A * 4/2000 Portman ................. A23L 1/296
424/601
6,827,945 B2 * 12/2004 Rosenbloom ........ A61K 36/185
424/434

(Continued)

FOREIGN PATENT DOCUMENTS

CA 2093573 * 1/1995

OTHER PUBLICATIONS

Website document entitled "Health911". Aug. 14, 2010. 3—pages. http://web.archive.org/web/20100814232301/http://www.health911.com/sore-throat.*

(Continued)

*Primary Examiner* — Chris R Tate
(74) *Attorney, Agent, or Firm* — Steptoe & Johnson LLP

(57) ABSTRACT

A therapeutic rinse for treating a sore throat. The therapeutic rinse may be stored in a self-heating container that is capable of reaching a temperature of at least 130 degrees Fahrenheit when activated. The therapeutic rinse includes a liquid composition having sodium chloride, water, and a variety of vitamins, minerals and herbs stored in the reservoir of the self-heating container. An antibiotic may also be included in the therapeutic rinse. Before use, the therapeutic rinse may be heated.

5 Claims, 1 Drawing Sheet

Related U.S. Application Data

(60) Provisional application No. 61/442,717, filed on Feb. 14, 2011.

(51) Int. Cl.

| | | |
|---|---|---|
| *A61K 36/81* | (2006.01) | |
| *A61K 36/53* | (2006.01) | |
| *A61K 45/06* | (2006.01) | |
| *A61K 36/185* | (2006.01) | |
| *A61K 8/92* | (2006.01) | |
| *A61K 8/97* | (2017.01) | |
| *A61K 8/19* | (2006.01) | |
| *A61K 9/00* | (2006.01) | |
| *A61K 9/08* | (2006.01) | |
| *A61M 31/00* | (2006.01) | |

(56) References Cited

U.S. PATENT DOCUMENTS

| | | | | |
|---|---|---|---|---|
| 8,709,505 B2* | 4/2014 | Boghossian | .......... | A61M 15/00 424/49 |
| 9,072,753 B1* | 7/2015 | Brown | .......... | A61K 36/63 |
| 2003/0206942 A1* | 11/2003 | Kulkarni | .......... | A61K 8/731 424/443 |
| 2005/0084459 A1* | 4/2005 | Reznick | .......... | A24B 15/00 424/48 |
| 2005/0152852 A1* | 7/2005 | Nishimura | .......... | A61K 8/361 424/50 |
| 2007/0178123 A1* | 8/2007 | Levenson | .......... | A61K 9/0053 424/400 |
| 2007/0218114 A1* | 9/2007 | Duggan | .......... | A61K 45/06 424/443 |
| 2012/0209177 A1* | 8/2012 | Boghossian | .......... | A61M 15/00 604/113 |
| 2013/0015204 A1* | 1/2013 | Gol | .......... | B65D 1/0238 222/129 |
| 2013/0274236 A1* | 10/2013 | Swart | .......... | A61K 9/0065 514/182 |
| 2014/0294990 A1* | 10/2014 | O'Connor | .......... | A61K 33/14 424/641 |
| 2016/0346322 A1* | 12/2016 | Martin | .......... | A61K 33/14 |

OTHER PUBLICATIONS

Website document entitled 'Dead Sea Benefits—General Health Facts'. 6 pages. Downloaded on Feb. 1, 2017. Obtained from http://www.deadsea.com/articles-tips/health-benefits/general-health-facts/.*

Website document entitled '20 Quick Facts About the Dead Sea'. 6 pages. Downloaded on Feb. 1, 2017. Obtained from http://www.sfsalt.com/20-dead-sea-facts.*

* cited by examiner

THERAPEUTIC RINSE

CROSS REFERENCES TO RELATED APPLICATIONS

This application is a continuation-in-part of U.S. patent application Ser. No. 13/372,356 filed Feb. 13, 2012, which claims the benefit of U.S. Application Ser. No. 61/442,717, filed Feb. 14, 2011, all of which are hereby incorporated by reference.

BACKGROUND

This invention relates to a therapeutic rinse for treating sore throats, mouth sores and/or minor gum infections. This invention also relates to a therapeutic rinse for use as a first aid disinfectant.

There are many home-remedies for treating the early signs of a sore throat, mouth sore and/or minor gum infection. However, these home-remedies are 1) not convenient when away from home, at work, at school, or traveling; 2) not as effective with one-to-two household ingredients; and 3) not consistent since the do-it-yourself home-made version can vary significantly. There are also commercially available products that suggest they can boost or support a person's immune system to help prevent illness, such as colds and sore throats. However, these home-remedies and commercially available products often require heating or mixing hot water at home to provide a more soothing effect.

What is needed is an out-of-home and in-home remedy that is more convenient, effective and consistent.

SUMMARY

Briefly, and in general terms, disclosed embodiments include a therapeutic rinse for treating a sore throat, mouth sore and/or minor gum infection including a self-heating container having a reservoir. The self-heating container is capable of reaching a temperature of at least 130 degrees Fahrenheit when activated. In use, the self-heating container may reach between about 130 and 150 degrees Fahrenheit upon activation of the self-heating container. In one embodiment, the self-heating container includes a cap that measures an ounce of liquid.

As an example, the therapeutic rinse includes a liquid composition having sodium chloride, water, vitamins, minerals, herbs and an antibiotic stored in the reservoir of the self-heating container. During use, the self-heating container is activated and the liquid composition is heated inside the reservoir. The temperature of the liquid composition inside the reservoir may reach about 130 degrees (+/−30 degrees) Fahrenheit.

In one embodiment, the liquid composition includes a ratio of about 7.5 mL of sodium chloride to about 180 ml of water. In another embodiment, the liquid composition includes a ratio of about 15 ml of sodium chloride to about 79 ml of water. Also, the liquid composition may include a total of about 180 mL (6 oz.) or about 90 ml (3 oz.). The liquid composition may include some or all of the following ingredients: sodium chloride (salt), vinegar or raw apple cider vinegar, honey, lemon juice, cayenne pepper, oregano oil, licorice root, slippery elm, and sage. The liquid composition may include about 10 mg to about 100 mg of antibiotic. In other embodiments, the liquid composition may include about 20 mg to about 200 mg of antibiotic or about 15 mg to about 150 mg of antibiotic. The antibiotic selected may be either Zithromiacin, Cephalexin, or other upper respiratory antibiotics. The specific measurements of the ingredients that form the liquid composition can vary depending on the desired results and taste of the liquid composition. It has been contemplated that the specific measurements and ratios given above may vary by about 30%.

Embodiments are also directed to a method of forming a therapeutic rinse. The method may include preparing a liquid composition having sodium chloride, water, vitamins, minerals and herbs. The liquid composition may also have an antibiotic. Further, the method includes a self-heating container having a reservoir, wherein the self-heating container is capable of reaching at least 130 degrees (+/−30 degrees) Fahrenheit. The liquid composition may be placed within the reservoir of the self-heating container and the reservoir of the self-heating container can be sealed with a cap or any tamper-proof device. In other embodiments, the liquid composition may be placed in a container such that the contents of the container can be heated or mixed with hot water.

DETAILED DESCRIPTION

Figure 1:
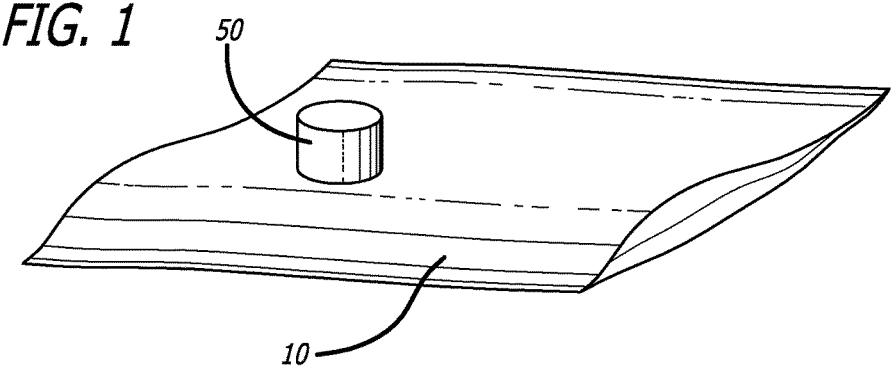
FIG. 1 depicts a perspective view of one embodiment of a pouch including a therapeutic rinse, wherein the pouch may be self-heating.
Figure 2:
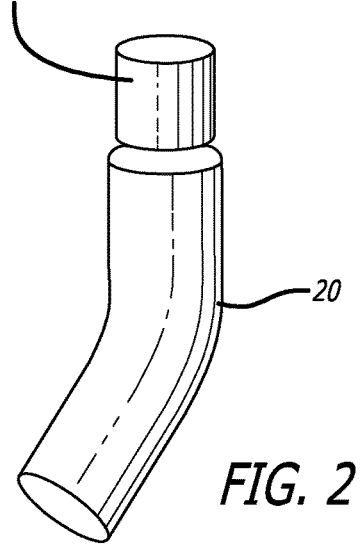
FIG. 2 depicts a perspective view of one embodiment of a flexible tube stick including a therapeutic rinse, wherein the flexible tube stick may be self-heating.
Figure 3:
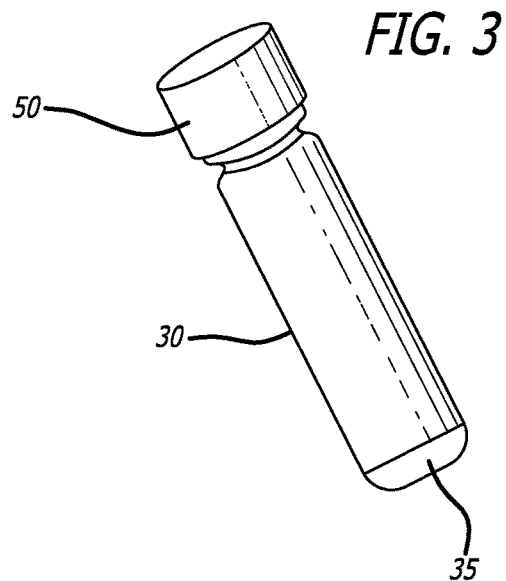
FIG. 3 depicts a perspective view of one embodiment of a bottle including a therapeutic rinse, wherein the bottle may be self-heating.
Figure 4:
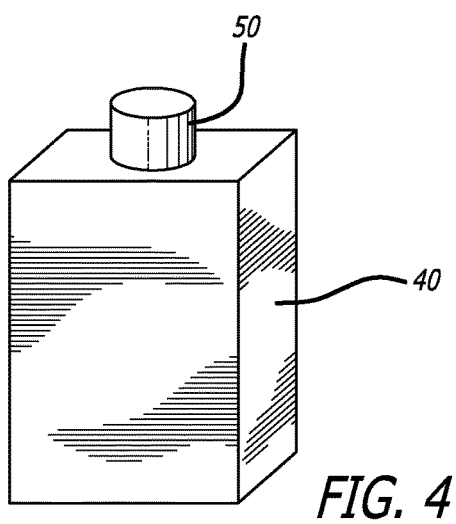
FIG. 4 depicts a perspective view of one embodiment of a self-heating carton including a therapeutic rinse wherein the carton may be self-heating.

Turning now to the figures, which are provided by way of example and not limitation, one example of a disclosed embodiment is a self-heating package that includes salt water, vitamins, minerals, herbs and an antibiotic rinse. Referring now to the drawings, wherein like reference numerals denote like or corresponding components throughout the drawings and, more particularly to FIGS. 1-5, there is shown different embodiments of a package for storing a therapeutic rinse.

As disclosed in more detail below, one embodiment is a therapeutic liquid or composition that can be used as a remedy for a sore throat, mouth sore and/or minor gum infection. In another embodiment, the therapeutic liquid or composition can be used to clean and disinfect minor scrapes and abrasions. In both of these embodiments, the therapeutic liquid is contained in a package that may be self-heating. However, it has been contemplated that the therapeutic rinse can be stored in a regular container that is not self-heating. In this embodiment, users could self-heat the contents if desired.

Therapeutic Rinse

The therapeutic rinse may be used to treat a viral or bacterial sore throat, mouth sore and/or minor gum infection. In one embodiment to treat and/or prevent a viral sore throat, commonly associated with the common cold, the therapeutic rinse has a liquid composition including a specific concentration of salt dissolved in water. In another embodiment the therapeutic rinse may be used to treat and/or prevent a bacterial infection, such as strep throat, and the therapeutic rinse may include a liquid composition including a concentration of salt and an antibiotic dissolved in water. Typically, signs of a bacterial infection consist of white patches, puss, green and/or yellow discharge. As used in this application, salt refers to sodium chloride. However, it has been contemplated that unrefined salt (sea salt), refined salt (table salt), and/or iodized salt can also be used. Also, water as used in this application can mean distilled water, filtered water or treated water.

One embodiment of a therapeutic rinse to treat a viral sore throat, mouth sore and/or minor gum irritation may include about 7.5 mL of salt to about 180 mL of water brought to a temperature of about 130 degrees Fahrenheit in a self-heating package or container. In another embodiment the therapeutic rinse may include about 15 mL of salt to about 79 mL of water. However, the temperature of the therapeutic rinse can range from 100 degrees Fahrenheit to about 150 degrees Fahrenheit. There is no medicinal treatment for a viral sore throat, only time and rest as a user's body fights the stages of what is known as the common cold. Therefore, there is no need for an antibiotic ingredient. However, if a user gargles with a high enough concentration of salt at the earliest sign of sore throat discomfort it can weaken the viral attack, thereby greatly decreasing the chances of getting the common cold; and if taken after the onset of a sore throat it can greatly decrease the duration/severity of the sore throat and common cold. Cells found in the mouth are made up of 70% water. These cells require water to function effectively. When high concentrations of salt are introduced to the mouth/throat, the water is extracted thereby isolating the virus and/or bacteria that is present and handicapping it from multiplying further. Water is essentially the fuel that feeds the cells, without it, the cells are compromised, and the virus is starved disabling it from multiplying. With repeated high concentration salt water rinses three times a day post-meals for a minimum two days viral cells can be eliminated remedying the sore throat. The subject therapeutic rinse consists of a high concentration of salt water in addition to a variety of vitamins and minerals to further combat the sore throat by introducing immunity building agents.

Bacterial cells that cause infections will be handicapped from multiplying when a high concentration of salt is introduced to the mouth/throat. A bacterial infection will also require an upper respiratory antibiotic rinse as well to combat the infection most effectively. Upper respiratory antibiotics are used in addition to a variety of vitamins, minerals and herbs to further combat the sore throat by introducing immunity building agents.

Experiments have been conducted and it was found that if a person gargles with this concentration of salt water heated to approximately 130 degrees Fahrenheit three (3) times a day at the onset of sore throat symptoms, post-meals, consistently for a minimum of 3 days, they will not allow the infected cells to reproduce and ultimately, the number of bacterial cells drastically diminishes. Use of this therapeutic agent helps to treat and prevent sore throats, mouth sores and minor gum infections.

Another embodiment of a therapeutic rinse used to treat a bacterial sore throat has a liquid composition that includes about 7.5 mL of salt to about 180 mL of water to about 1 mg to about 20 mg of Zithromiacin brought to a temperature of about 130 degrees Fahrenheit. In certain embodiments, 5 mg, 10 mg, 15 mg and 20 mg of Zithromiacin is used in combination with the salt and water mixture. The temperature of the therapeutic rinse may range from about 100 degrees Fahrenheit to about 150 degrees Fahrenheit. Zithromiacin is an antibiotic used for treating upper respiratory infections. Although about 1 mg to about 20 mg of Zithromiacin is preferred, the amount of Zithromiacin may be about 1 mg to about 200 mg.

Normally antibiotics are used in the treatment of upper respiratory tract infections, which may include a sore throat. In most cases, if the upper respiratory tract infection is treated in its early stages with the antibiotic therapeutic rinse described above, water will move out of the bacterial cells and the antibiotic therapeutic rinse will be introduced to it thereby destroying the bacterial cells in its weakest state. In one experiment, gargling the antibiotic therapeutic liquid three (3) times a day, consistently for 3 days, destroyed a majority of the bacterial cells.

Antibiotics are the substances which kill or inhibit the growth of bacteria. The following antibiotics (and any new upper respiratory antibiotics that may be developed) may be used in the liquid composition in addition to or in place of Zithormiacin: Azithromycin, Penicillin, cephalosporin, polymixin, quinolone, sulfonamides; Aminoglycoside, macrolide and tetracycline; cyclic lipopeptide (daptomycin), glycylcycline (tigecycline), and oxazolidinone (linezolid); Tigecycline, Erythromycin, Blephamide, Cefadroxil, Cefepime, Cefoxitin, cephalosporin, Cephazolin, cephalosporin, Chloramphenicol, Chlorsig, Clarithromycin, Clindamycin, Colistin, Dicloxacillin, Duricef, Floxin, Levaquin, Mefoxin, Minocycline, Norfloxacin, Omnicef, Pneumovax, Rifampin, Staphlex, Targocid, Tetracycline, Vancocin, Ambisome, Ampicillin, Bactroban, Cefaclor, Cefdinir, Cefixime, Cefpodoxime, Cephalexin, Ceptaz, Chloromycetin, Ciprofloxacin, Clindagel, Cloxacillin, Co-trimoxazole, Doxycycline, Erythromycin, Gatifloxacin, Levofloxacin, Meronem, Zymar, Cephradine, Cefotetan, Cefprozil, Loracarbef, Cefdinir, Cefoperazone, Cefotaxime, Ceftazidime, Ceftibuten, Ceftizoxime, Ceftriaxone, Ciprofloxacin, Gatifloxacin, Moxifloxacin, Ofloxacin, Ampicillin, Nafcillin, Penicillin VK, Piperacillin/tazobactam, Ticarcillin/clavulanate, Ampicillin/sulbactam, Amoxicillin/clavulanate, Penicillin G, Piperacillin, Ticarcillin, Doxycycline, Bacitracin, Mupirocin, Metronidazole, Aztreonam, Sulfa trimethoprim, Dapsone, Ertapenem, Imipenem, Meropenem, Metronidazole, Nitrofurantoin, Rifaximin, Tinidazole, Quincipristin, Dalfoprictin, Telithromycin, Sulfacetamide, Tazarotene, Amikacin, Gentamicin, Neomycin, Streptomycin, Tobramycin, Bacitracin, Mupirocin, Polymixin, and Silver sulfadiazine.

As an example, and not by way of limitation, a 6 oz. portion of the therapeutic rinse may include 7.5 mL (1½ Teaspoon) Dead Sea Salt, 5 mL (1 Teaspoon) Apple Cider Vinegar, 5 mL (1 Teaspoon) lemon concentrate or an equivalent amount of lemon juice, 1.25 mL (¼ Teaspoon) Cayenne Pepper, 2.5 mL (½ Teaspoon) Licorice Root, 112 mg (4 drops) Concentrated Oregano Oil, 5 mL (1 Teaspoon) Honey, and 10 mL of a blend of ingredients described below. In one embodiment, 0.07 mL of colloidal silver may also be included. Also, a preservative to allow shelf stability may be included in one embodiment. In one embodiment the 10 mL blend includes equal parts or zinc, slippery elm, *Echinacea*, B-complex, and valerian root. In another embodiment, the 10 mL blend may include equal parts of silver sulfadiazine, zinc, slippery elm, flavor enhancer, tumeric, and amino acids. A flavor enhancer, such as cherry or strawberry, may be used as desired in any of the described embodiments. These ingredients are mixed with water to create the 6 oz. portion of the therapeutic rinse. These concentrations can be scaled up or down to create 4 oz., 8 oz., 10 oz., 12 oz., or larger portions of the therapeutic rinse. Also, in other embodiments, the individual measurements of the listed ingredients may vary by 10%. Furthermore, all approximation given in this specification may vary by 10%. The specific amount of ingredients used to create the therapeutic composition may vary depending on desired results or taste. In addition, any of the ingredients listed above may be used in any combination with each other to create a therapeutic rinse.

In other embodiments, the 10 mL blend of ingredients can include any of the following vitamins, minerals, herbs and other ingredients: Amino Acids, Antioxidants, B Vitamins, C Vitamins, D Vitamins, Calcium, Enzymes, Garlic products, Bilberry, Black Cohosh, Cascara Sagrada, Cinnamon, Dandelion Root, *Echinacea, Ginko Biloba*, Ginseng complex, Green tea extract, Hawthorn Berries, Milk Thistle, Noni, Saw Palmetto, St. John's Wort, Super Guarana, Tumeric/Curcumin with Tumeric Extract, Valerian Root, Chromium Picolinate, Iron, Kelp, Magnesium, Potassium, Selenium, Zinc, Slippery Elm, Paprika, sage (or sage extract), and/or natural and organic flavor enhancers as desired, and/or Colloidal Silver.

By way of example, and not by way of limitation, one embodiment of the therapeutic rinse may not include an antibiotic, Colloidal silver, or both. In such an embodiment, the blend for the therapeutic rinse may include any or all of the following ingredients: salt, vinegar, honey, lemon, cayenne pepper, oregano oil, licorice root, slippery elm, and sage. It has been contemplated that an antibiotic or Colloidal silver could be added to such a blend of ingredients.

In yet another embodiment, the therapeutic rinse may even be in a spray or inhaler form. Also, the therapeutic rinse can be in tablet or powder form that can then be added to warm water (or temperature of choice) for gargling and rinsing as described above. The therapeutic rinse embodiment will allow the user to choose the most convenient option with the liquid pouch that self-heats upon activation for prompt action/use regardless of whereabouts; and a more staple version in a tablet or powder form to always keep on hand at the home/office for use when the need arises. The tablets or powder will come in a typical plastic tube case, that may be biodegradable. The tablets or powder form may include salt, a variety of vitamins, minerals and herbs. Also, the tablets or powder form may also contain an antibiotic. Both the tablet or powder form will be designed to dissolve in water to create a mixture for treating sore throats, mouth sores, minor gum infections or for use as a first aid disinfectant. In one embodiment, each tablet or tablespoon of powder may include about 5 mg to 20 mg of an antibiotic and may contain a flavor enhancer. The tablet or powder version may dissolve in water. Also, the therapeutic rinse, tablet, or powder versions may be packaged in a single-serve Pod such that it can easily be used with a coffee machine, espresso machine, or similar machines, such as a Keurig K-Cup® machine.

Timely use of the antibiotic therapeutic rinse may kill the bacterial and other germs before a more severe cold or sore throat develops. The embodiments of the therapeutic rinse described herein provide an effective method to kill bacteria versus current over-the-counter remedies that numb the throat region for temporary pain relief. Furthermore, the self-heating container serves as a convenient shelf stable product for a quick remedy that may be used anywhere, anytime immediately—for the unexpected onset of a sore throat symptom—at school, work, in route on business, on vacation, etc. Since the packaging offers a self-heating feature for a warm gargle, a more effective absorption rate occurs for best results. Also, the all-in-one packaging allows the user to be thorough and consistent in gargling three times a day regardless of a busy schedule. It is recommended that user activate the package for a quick heat, shake, gargle one package (includes up to five gargles) in the morning, repeat in the afternoon, and repeat in the evening post meals.

Disinfecting Rinse

In another embodiment, a disinfecting rinse is used to clean, disinfect and treat minor scrapes and abrasions to guard against bacterial infections. The disinfecting rinse can be used when other first aid kits or remedies are not available. This embodiment is intended as a portable emergency rinse that is convenient for school, travel, sports, workplace, and the like. The disinfecting rinse can include a cleaning embodiment and a treating embodiment.

One embodiment for a disinfecting rinse is a liquid composition that includes any type of soap or derivative of fatty acid and water that is brought to a temperature of about 130° F. Raising the temperature to about 130° F. provides improved results. However, the temperature of the disinfecting rinse may range from about 100° F. to about 150° F.

Another embodiment for the disinfecting rinse include a liquid composition including salt, water and an antibiotic powder. An intricate ratio of each element to prove both safe and effective in disinfecting and topically treating minor cuts or abrasions may be about 7.5 mL of salt to about 180 mL of water to about 1 mg to about 20 mg of Cephalexin. The ration may be about 15 mL of sodium chloride to about 79 mL of water in another embodiment. Cephalexin is an antibiotic typically used to treat bacterial infections of the skin. Although about 1 mg to about 20 mg of Cephalexin is preferred, the amount of Cephalexin may be about 1 mg to about 200 mg. It has also been contemplated that other antibiotics from the list described above can be included in place of or in addition to Cephalexin. This liquid composition is then brought to a temperature of about 130° F. However, the temperature of the disinfecting rinse may range from about 100° F. to about 150° F.

The disinfecting rinse provides a portable means to effectively clean, disinfect and treat minor cuts and abrasions, and guard against bacterial infection. The disinfecting rinse offers a shelf stable product to store in critical areas, such as a car, lockers, office, travel pack, and the like, so that it is available in the moment of need with no compromise to remedy.

Many antibiotic first-aid products contain combinations of antibiotics to make them effective against a broad range of bacteria. When treating a wound, it is not enough to simply apply a topical antibiotic. The wound must first be cleaned with soap and water and patted dry. Then, topical antibiotics help prevent infections caused by bacteria that get into minor cuts, scrapes, and burns. Treating minor wounds with antibiotics allows quicker healing. If the wounds are left untreated, the bacteria will multiply, causing pain, redness, swelling, itching, and oozing. Untreated infections can eventually spread and become much more serious.

Figure 5:
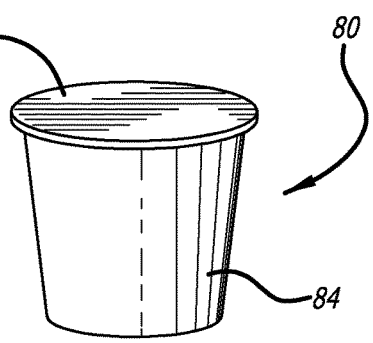
FIG. 5 depicts a perspective view of one embodiment of a container including a therapeutic rinse.

Packaging:

As mentioned above, in one embodiment, the liquid composition of the therapeutic rinse and disinfecting rinse is packaged in a container, such as a pouch 10 (FIG. 1), flexible tube stick 20 (FIG. 2), bottle 30 (FIG. 3), carton 40 (FIG. 4), or pod 80 (FIG. 5). Any type of container may be used and the containers may or may not be self-heating containers. The containers may have reservoirs for holding the rinse ranging from 4 oz., 6 oz., 8 oz., or larger in size. If self-heating, the containers may each have an activation zone or area such as a flexible wall, tab, screw that when pressed, pulled, or turned by the user activates the self-heating container. The activation zone may be located anywhere on the self-heating container. By way of example and not by way of limitation, an activation portion 35 is shown near the bottom of the bottle 30 shown in FIG. 3. Once the package is activated, the package can self-heat to a temperature of about 130° F. (+/−30 degrees) for a warm temperature rinse. An activated package can also be configured to reach temperatures of about 150° F. In use, the warm temperature of the liquid composition offers greater absorption. For a treatment, a user should activate the container then shake the self-heating container to dissolve the salt and antibiotic powder in the water. The user may need to shake the self-heating container well before each gargle. In one embodiment, a cap 50 that screws on and off of the self-heating container 10, 20, 30 or 40 measures exactly one (1) Tablespoon of liquid that can be used for each gargle rinse. The self-heating container packaging may be biodegradable so that it is environmentally responsible.

In another embodiment, the pouch 10 may be a pod that does not include a cap 50 and has a membrane filter similar to a coffee filter. In such an embodiment, the pod is not self-heating and may be used in a coffee machine, espresso machine, or the like. Still further, a container for storing the therapeutic rinse may have a shape and structure that is capable of being used in existing coffee machines or the like. In this way, the powder version of the therapeutic rinse (without liquid) may be placed in a universal pod filter that may be used with any single-serve coffee machine or the like to create a warm therapeutic rinse. It has also been contemplated that the therapeutic rinse may be in a concentrated form such that it is a liquid that can be mixed with additional water to create a therapeutic rinse. Further, the powder version of the therapeutic rinse in membrane filter container may be added to a cup of hot water to create a therapeutic rinse. The pod or container 80 for storing the therapeutic rinse in a concentrated liquid form or a powder form is shown in FIG. 5. In this embodiment, the container 80 may have an appropriate shape to be used with a Keurig K-Cup machine or similar machine. The container 80 may have a top 82 that is removable or can be pierced or broken. A bottom portion 84 of the container 84 may be formed of a plastic or similar material and can have a rounded end or a square-shaped end. The bottom portion 84 may also be a membrane.

Self-heating containers are known to those of ordinary skill in the art. Self-heating containers may include various mechanisms for creating an exothermic reaction by mixing various chemicals. In general, the self-heating container can be activated by the user using manual force. For instance, force can be applied to an activator located on the self-heating container, such as a moveable part or barrier. Once the activator is activated, mechanisms within the self-heating container allow chemicals to mix and react, allowing the temperature of the mixed concentration to increase, and thereby heating the contents in a reservoir of the self-heating container. Examples of self-heating containers are shown in U.S. Publication Nos. 2010/0224510 and 2009/0078711. Some self-heating containers are activated by adding water onto an ionic solid, such as calcium oxide or calcium chloride. Examples of this type may be found in U.S. Pat. No. 5,626,022 (Scudder et al.), U.S. Pat. No. 5,388,565 (Ou), and U.S. Pat. No. 4,773,389 (Hamasaki).

Self-heating containers may also include the mechanism of mixing acids and bases. An example of this type of self-heating container is U.S. Pat. No. 5,935,486 (Bell et al.) that involves mixing of various organic and inorganic acids and bases.

Another type of self-heating container uses oxidation-reduction reactions occurring in the aqueous phase. Examples of this type include U.S. Pat. No. 5,517,981 (Taub et al.) in which magnesium is mixed with cupric chloride in the presence of water and U.S. Pat. No. 3,998,749 (Hydro et al.) where aluminum and cupric chloride are mixed in a mixture of aqueous and organic solvents.

Yet another type of self-heating container uses solid phase self-propagating high-temperature synthesis (SHS) reactions, which include oxidation-reduction processes in the solid-state (such as thermite reactions). Examples include U.S. Pat. No. 4,506,654 (Zellweger et al.), U.S. Pat. No. 4,819,612 (Okamoto et al.), U.S. Pat. No. 4,949,702 (Suzuki et al.), U.S. Pat. No. 5,020,509 (Suzuki et al.), and U.S. Pat. No. 5,220,908 (Iizuna et al.). In all of these examples, the fuel is a mixture of a metal or alloys, such as silicon or ferrosilicon and a metal oxide, such as ferric oxide or cupric oxide. These reactions are basically redox reactions between metals or semimetals and metal oxide, such as aluminum, silicon and ferric oxide.

Any of these known types of self-heating containers may be used to heat the therapeutic rinse and/or disinfecting rinse. Furthermore, any new type of self-heating container may also be used with the above embodiments of the therapeutic rinse and/or disinfecting rinse.

Thus, it will be understood by those of skill in the art that changes may be made to the present invention, and that changes in its use may also be made, without departing from the spirit of the invention, which is defined in the following claims.

I claim:

1. A method for treating a sore throat in a subject in need thereof, the method comprising gargling by the subject an effective amount of a therapeutic rinse formulation, wherein the therapeutic rinse formulation is prepared by a process comprising:

combining about 1.5 teaspoons of Dead Sea Salt, about 1 teaspoon of honey, about 1 teaspoon of lemon juice or concentrate thereof, and about 0.5 teaspoon of licorice root extract to obtain a composition, and mixing the composition in about 6 ounces of water to obtain the therapeutic rinse formulation.

2. The method of claim 1, wherein the composition further includes a flavor enhancer.

3. The method of claim 1, wherein the composition further includes oregano oil or concentrate thereof and vinegar.

4. The method of claim 1, wherein the composition is in powder form.

5. The method of claim 1, wherein the water is heated to at least 100 degrees Fahrenheit.

* * * * *